(12) United States Patent
Wang et al.

(10) Patent No.: US 6,232,366 B1
(45) Date of Patent: May 15, 2001

(54) PRESSURE SENSITIVE CONDUCTIVE ADHESIVE HAVING HOT-MELT PROPERTIES AND BIOMEDICAL ELECTRODES USING SAME

(75) Inventors: DanLi Wang, Maplewood; Peter A. Stark, Cottage Grove; Albert I. Everaerts, Oakdale, all of MN (US)

(73) Assignee: 3M Innovative Properties Company, Saint Paul, MN (US)

(*) Notice: Subject to any disclaimer, the term of this patent is extended or adjusted under 35 U.S.C. 154(b) by 0 days.

(21) Appl. No.: 09/328,334

(22) Filed: Jun. 9, 1999

(51) Int. Cl.$^7$ ................ H01B 1/06; C09J 9/02; C09J 133/04; A61L 24/00
(52) U.S. Cl. ............ 523/111; 252/500; 156/327; 600/391; 424/448; 428/41.5
(58) Field of Search ............... 252/500; 156/327; 156/322; 525/209, 221; 523/103, 111; 600/391; 424/448; 428/41.5

(56) References Cited

U.S. PATENT DOCUMENTS

| Re. 24,906 | 12/1960 | Ulrich | 206/59 |
|---|---|---|---|
| Re. 33,353 | 9/1990 | Heinecke | 428/40 |
| 2,973,286 | 2/1961 | Ulrich | 117/122 |
| 3,389,827 | 6/1968 | Abere et al. | 220/53 |
| 4,112,213 | 9/1978 | Waldman | 526/279 |
| 4,152,189 | 5/1979 | Guerin et al. | 156/331 |
| 4,310,509 | 1/1982 | Berglund et al. | 424/28 |
| 4,323,557 | 4/1982 | Rosso et al. | 424/28 |
| 4,524,087 | 6/1985 | Engel | 427/2 |
| 4,539,996 | 9/1985 | Engel | 128/640 |
| 4,554,924 | 11/1985 | Engel | 128/640 |
| 4,619,979 | 10/1986 | Kotnour et al. | 526/88 |
| 4,715,382 | 12/1987 | Strand | 128/640 |
| 4,732,808 | 3/1988 | Krampe et al. | 428/355 |
| 4,771,783 | 9/1988 | Roberts | 128/640 |
| 4,843,134 | 6/1989 | Kotnour et al. | 526/318.4 |
| 4,846,185 | 7/1989 | Carim | 128/641 |
| 4,848,353 | 7/1989 | Engel | 128/640 |
| 4,849,224 | 7/1989 | Chang et al. | 424/434 |
| 4,855,294 | 8/1989 | Patel et al. | 514/212 |
| 4,917,928 | 4/1990 | Heinecke | 428/41 |
| 4,917,929 | 4/1990 | Heinecke | 428/41 |
| 5,012,810 | 5/1991 | Strand et al. | 128/640 |
| 5,133,356 | 7/1992 | Bryan et al. | 128/640 |
| 5,230,701 | 7/1993 | Meyer et al. | 602/76 |
| 5,433,892 | * 7/1995 | Czech | 252/500 |
| 5,489,624 | 2/1996 | Kantner et al. | 524/376 |
| 5,505,200 | 4/1996 | Takaki | 128/640 |
| 5,506,059 | 4/1996 | Robbins et al. | 428/457 |
| 5,637,646 | 6/1997 | Ellis | 525/309 |
| 5,670,557 | 9/1997 | Dietz et al. | 522/184 |
| 5,804,610 | 9/1998 | Hamer | 522/182 |
| 5,905,099 | * 5/1999 | Everaerts et al. | 522/126 |

FOREIGN PATENT DOCUMENTS

| 0051935 | 5/1982 | (EP) . |
|---|---|---|
| 0341875 | 11/1993 | (EP) . |
| WO89/07951 | 9/1989 | (WO) . |
| WO99/42536 | 8/1999 | (WO) . |

OTHER PUBLICATIONS

"Mixing in Single-Screw Extruders", Mixing in Polymer Processing, ed. Chris Rauwendaal (Marcel Dekker Inc.: New York (1991) pp. 129, 176–177; 185–186.

* cited by examiner

*Primary Examiner*—Mark Kopec
(74) *Attorney, Agent, or Firm*—John A. Burtis (57) ABSTRACT

A skin-compatible, hot-melt processible, pressure sensitive adhesive is disclosed. A thermo-reversible cross-linking is achieved, permitting advantages in processcibility and the reduction of waste.

22 Claims, 2 Drawing Sheets

PRESSURE SENSITIVE CONDUCTIVE ADHESIVE HAVING HOT-MELT PROPERTIES AND BIOMEDICAL ELECTRODES USING SAME

FIELD OF THE INVENTION

The invention relates to a conductive pressure sensitive adhesive that has hot melt properties (or that can be hot-melt processed) suitable for as an ionically conductive pressure sensitive adhesive for a biomedical electrode.

BACKGROUND OF THE INVENTION

Biomedical electrodes are used for diagnostic and therapeutic purposes including electrocardiographic monitoring and diagnosis, electrosurgery, iontophoretic (electrically enhanced) transdermal delivery of drugs, and defibrillation. In their most basic form, these electrodes have a conductive medium contacting mammalian skin and a means for electrical communication interacting between the conductive medium and electrical diagnostic, therapeutic, or electrosurgical equipment.

The conductive medium used in these electrodes is generally an ionically conductive adhesive or gel. A conductive adhesive composition which both serves to adhere a biomedical electrode to skin and to establish an electrical connection between skin and an electrical medical apparatus should desirably have multiple characteristics which are difficult to achieve in one composition. At minimum, the composition should have the characteristics of a good medical adhesive and those of a good ionic conductor. A good medical pressure-sensitive adhesive needs to be dermally non-irritating, compliant and tacky enough so as to wet onto skin and adhere, and sufficiently cohesive both to resist shear and peel forces and to pull away from skin without leaving a residue. To optimize electrical performance, low impedance at the interface of the composition and the skin is desirable.

It is known that ionically conductive adhesives can be compounded from a polar polymeric network which is plasticized with a humectant material such as glycerin or poly(ethylene glycol). Water, a salt, or a pharmaceutical can also be included depending on the application. Generally a relatively thick layer of adhesive or gel is used (10 to 100 mil (0.25 to 2.5 mm) or greater).

Much work has been done in recent years to optimize conductive adhesives for biomedical applications, to achieve better properties in one area without having to compromise excessively in another. One area that has not had as much development is the preparation of conductive adhesives that are melt processable after the polymeric material has been formed for use in the manufacture of a biomedical electrode. The available materials are viscous, cohesive, and non-water soluble. Once placed by polymerization onto a backing material, they cannot be practically reprocessed or recycled. Any adhesive that is placed on material, i.e., the "weed" which is cut away during the automated die cutting of bioelectrodes, must now be discarded as waste.

In addition, known processing methods involve polymerization on the substrate or coating from a carrier solvent (organic or water). These processes are typically slow and can involve difficult drying steps because of the thickness of the electrode material.

SUMMARY OF THE INVENTION

What the art needs is a skin-compatible, non-water soluble, pressure sensitive adhesive, preferably ionically conductive, to be formulated in a manner which permits the recycling of such material after application to a substrate. The possibility to coat thick layers of conductive adhesive at high process speeds is also economically attractive. Any drying step otherwise needed in prior art processing is eliminated.

The present invention solves these current problems in the art by providing a conductive adhesive with all the desired properties discussed in the paragraph immediately above. Further, the conductive adhesive of the present invention is additionally melt-processable at a suitably low temperature to reduce manufacturing costs. As a result of the use of low temperatures, there is no need to rehydrate the adhesive after processing. The adhesive can be spread in a molten state onto a substrate, such as an electrode backing material. Thereafter, any waste material can be recovered and reprocessed by the application of mild heat. Because the adhesive is melt-processible before and after electrode formation, the adhesive can be used in manufacturing electrodes using a wider variety of methods so that initial waste is minimized.

The present invention concerns a formulation which is skin-compatible, non-water soluble, cohesive, and conductive, and yet is melt-processable because of a thermo-reversible crosslinking mechanism.

Compared to currently used application and curing methods, use of the present invention can also provide the benefits of lower residual monomers, or a higher coating speed. Compared to methods that require exposure of the adhesive to UV radiation, the adhesive is easier to coat in greater thickness because no light penetration is necessary such as required for UV radiation polymerized or crosslinked adhesives.

Formulations suitable for low temperature melt-processible ionically conductive pressure sensitive adhesives (PSAs) for skin application according to the present invention can be made from a copolymer of alkyl acrylate monomers and hydrophilic comonomers, polymerized either through thermal polymerization or UV polymerization. This can be performed even in the presence of humectants and/or hydrophilic plasticizers such as glycerin and/or polyethylene glycol (PEG). The plasticized polymer can thereafter be melt-processed with a mixture having surfactant, amine containing polymeric ionic crosslinker, a salt to improve ionic conductivity properties (usually KCl) and water. The temperature of melt processing ranges from about 50° C. to about 100° C. and more preferably from about 55° C. to about 85° C. to make thick layers useful in biomedical electrodes as the conductive medium. Alternatively, the material can be used in other ionically conductive and pressure-sensitive adhesive articles.

Briefly, one aspect of the present invention provides a skin-compatible, hot-melt processible, pressure sensitive adhesive, comprising:

between about 30 and about 45 parts by weight of a copolymer comprised of between about 30 to 45 parts by weight of an (meth)acrylate ester monomer having $C_4$–$C_{20}$ alkyl chains, and between about 55 to 70 parts by weight of an acidic comonomer;

between about 0 and about 35 parts by weight of a hydrophilic plasticizer;

between about 20 and about 40 parts by weight of water, between about 0 and about 3 parts by weight of a water soluble salt, between about 10 and about 20 parts by weight of a surfactant, and between about 0.5 and about 10 parts by weight of a polymer having amine functionality.

Another aspect of the present invention provides a method for preparing skin-compatible, hot-melt processable, pressure sensitive adhesive, comprising the steps of:

a) preparing a mixture of ethylenically unsaturated monomers comprising:
   between about 30 and about 45 parts by weight of an (meth)acrylate ester monomer having $C_4$–$C_{20}$ alkyl chains, and
   between about 55 and about 70 parts by weight of an acidic comonomer;
b) mixing between about 30 and about 45 parts by weight of the mixture of the ethylenically unsaturated monomers with between about 0 and about 35 parts by weight of a hydrophilic plasticizer so as to form a hydrophilic plasticizer/monomer mixture;
c) polymerizing the monomers to form a polymer matrix containing the plasticizer;
d) blending an additive mixture into the polymer matrix, the additive mixture comprising
   between about 20 and about 40 parts by weight of water,
   between about 0 and about 3 parts by weight of a water soluble salt,
   between about 10 and about 20 parts by weight of a surfactant, and
   between about 0.5 and about 10 parts by weight of a polymer having amine functionality,
so as to form a skin-compatible hot-melt processable, ionically conductive, pressure sensitive adhesive.

Yet another aspect of the present invention provides a method for preparing skin-compatible, hot-melt processable, pressure sensitive adhesive, comprising the steps of:

a) preparing a mixture of ethylenically unsaturated monomers comprising:
   between about 30 and about 45 parts by weight of an (meth)acrylate ester monomer having $C_4$–$C_{12}$ alkyl chains, and
   between about 55 and about 70 parts by weight of an acidic comonomer;
b) mixing between about 30 and about 45 parts by weight of the mixture of ethylenically unsaturated monomers with between about 0 and about 35 parts by weight of a hydrophilic plasticizer, between about 10 and about 30 parts by weight of water, between about 0 and about 3 parts by weight of a water soluble salt, and between about 0 and about 7 parts by weight of a surfactant, so as to form a hydrophilic plasticizer/monomer/surfactant/water mixture;
c) polymerizing of the monomers to form a polymer matrix containing plasticizer, water, and surfactant;
d) blending an additive mixture into the polymer matrix, the additive mixture comprising
   between about 1 and about 3 parts by weight of a water soluble salt,
   between about 10 and about 30 parts by weight of water,
   between about 10 and about 13 parts by weight of a surfactant, and
   between about 0.5 and about 10 parts by weight of a polymer having amine functionality,
so as to form a skin-compatible hot-melt processable, ionically conductive, pressure sensitive adhesive.

The skin-compatible, hot-melt processable, pressure sensitive adhesives of the invention can be used in a variety of applications where pressure sensitive adhesives are industrially or commercially applied in the manufacture of tapes, adhesive substrates, and the like. They are particularly useful to prepare various constructions of biomedical electrodes and pharmaceutical delivery devices.

Another aspect of the present invention is a biomedical electrode comprising skin-compatible, hot-melt processable, ionically conductive, pressure sensitive adhesive of the invention.

Another aspect of the invention is a pharmaceutical delivery device comprising a skin-compatible, hot-melt processable, pressure sensitive adhesive of the invention.

As used herein in this application:

"pressure-sensitive adhesive" or "PSA" refers to a viscoelastic material that possesses the following properties: (1) aggressive and permanent tack, (2) adherence with no more than finger pressure, (3) sufficient ability to hold onto a substrate, and (4) sufficient cohesive strength to be removed cleanly from the substrate;

"(meth)acrylate monomers" are acrylic acid esters or methacrylic acid esters of non tertiary alcohols, the alcohols preferably having about 4 to 20 carbon atoms;

"acidic comonomers" are ethylenically unsaturated, free radically reactive monomers having carboxylic, sulfonic or phosphonic acid functionality and are copolymerizable with the (meth)acrylate monomers.

A feature of the invention is the adhesive having melt-processing properties to assist manufacturing and recycling of the unused adhesive.

An advantage of the invention is the reduced cost of manufacturing because of the melt-processing of the adhesive.

Further features and advantages are discussed below using the drawings and description of embodiments of the invention.

BRIEF DESCRIPTION OF THE DRAWINGS

The invention will be further described with reference to the drawing wherein corresponding reference characters indicate corresponding parts throughout the several views of the drawing, and wherein.

EMBODIMENTS OF THE INVENTION (Meth)acrylate Monomers

The conductive adhesives of the present invention contain at least one monofunctional unsaturated monomer selected from the group consisting of (meth)acrylate esters of non-tertiary alkyl alcohols, the alkyl groups of which comprise from about 4 to about 20, preferably about 4 to about 12 carbon atoms; and mixtures thereof. Preferred (meth) acrylate monomers have the following general Formula (I):

Formula (I)

wherein $R^1$ is H or $CH_3$, the latter corresponding to where the (meth)acrylate monomer is a methacrylate monomer. $R^2$ is broadly selected from linear, branched, aromatic, or cyclic hydrocarbon groups. Preferably, $R^2$ is a linear or branched hydrocarbon group. The number of carbon atoms in the hydrocarbon group is preferably about 4 to about 20, and more preferably about 4 to about 12. When $R^2$ is a hydrocarbon group, it can also include heteroatoms (e.g., oxygen or sulfur). Glass transition temperature (Tg) of a homopolymer or copolymer of (meth)acrylate monomers should not be so high as to deny the possibility of pressure sensitive adhesive properties to the fully blended composition of the invention. Preferably, the Tg should not exceed 50° C. and more preferably less than about 10° C.

Examples of suitable (meth)acrylate monomers useful in the present invention include, but are not limited to, benzyl methacrylate, n-butyl acrylate, n-butyl methacrylate, cyclohexyl acrylate, cyclohexyl methacrylate, decyl acrylate, 2-ethoxy ethyl acrylate, 2-ethoxy ethyl methacrylate, 2-ethylhexyl acrylate, n-hexadecyl acrylate, n-hexadecyl methacrylate, hexyl acrylate, isoamyl acrylate, isobornyl acrylate, isobornyl methacrylate, isobutyl acrylate, isodecyl acrylate, isodecyl methacrylate, isononyl acrylate, isooctyl acrylate, isooctyl methacrylate, isotridecyl acrylate, lauryl acrylate, lauryl methacrylate, 2-methyl butyl acrylate, 4-methyl-2-pentyl acrylate, 1-methylcyclohexyl methacrylate, 2-methylcyclohexyl methacrylate, 3-methylcyclohexyl methacrylate, 4-methylcyclohexyl methacrylate, octadecyl acrylate, octadecyl methacrylate, n-octyl acrylate, n-octyl methacrylate, 2-phenoxy ethyl methacrylate, n-tetradecyl acrylate, n-tetradecyl methacrylate, and mixtures thereof. Particularly preferred are the alkyl (meth)acrylate monomers.

Examples of preferred alkyl (meth)acrylate monomers are those in which the alkyl groups comprise from about 4 carbon atoms to about 12 carbon atoms and include, but are not limited to, n-butyl acrylate, 2-ethylhexyl acrylate, isooctyl acrylate, isononyl acrylate, isodecyl acrylate, and mixtures thereof. Optionally, other vinyl monomers and alkyl (meth)acrylate monomers which, as homopolymers, have a Tg greater than 10° C., such as methyl acrylate, methyl methacrylate, ethyl acrylate, isobornyl acrylate, vinyl acetate, styrene, and the like, can be utilized in conjunction with one or more of the alkyl (meth)acrylate monomers and copolymerizable monomers, provided that the Tg of the resultant (meth)acrylate copolymer is less than about 10° C.

As identified above, the copolymer includes from about 30 to about 45 parts by weight of (meth)acrylate monomer. Preferably, that amount is from about 38 to about 43 parts by weight.

Acidic Comonomers

Useful acidic comonomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, β-carboxyethyl acrylate, 2-sulfoethyl methacrylate, styrene sulfonic acid, 2-acrylamido-2-methylpropane sulfonic acid, vinyl phosphonic acid, and the like, and mixtures thereof. Due to their availability and effectiveness in reinforcing (meth)acrylate pressure sensitive adhesives, particularly preferred acidic monomers are the ethylenically unsaturated carboxylic acids, most preferably acrylic acid or β-carboxyethyl acrylate.

Minor amounts of monomers copolymerizable with the (meth)acrylate monomers and acidic monomers can be used. Examples of such monomers include (meth)acrylamides, vinyl esters and N-vinyl lactams.

As identified above, the copolymer includes from about 55 to about 70 parts by weight of acidic monomer. Preferably, that amount is from about 57 to about 62 parts by weight.

Initiators

A free radical initiator is preferably added to aid in the copolymerization of the (meth)acrylate comonomers and acidic comonomers. The type of initiator used depends on the polymerization process. Photoinitiators which are useful for polymerizing the polymerizable mixture of monomers include benzoin ethers such as benzoin methyl ether or benzoin isopropyl ether, substituted benzoin ethers such as 2-methyl-2-hydroxypropiophenone, aromatic sulfonyl chlorides such as 2-naphthalenesulfonyl chloride, and photoactive oxides such as 1-phenyl-1,1-propanedione-2-(o-ethoxycarbonyl)oxime. An example of a commercially available photoinitiator is IRGACURE 651 (2,2-dimethoxy-1,2-diphenylethane-1-one, commercially available from Ciba-Geigy Corporation,). Generally, the photoinitiator is present in an amount of about 0.005 to 1 weight percent based on the weight of the copolymerizable monomers. Examples of suitable thermal initiators include AIBN (2,2'-azobis(isobutyronitrile), hydroperoxides, such as tert-butyl hydroperoxide, and peroxides, such as benzoyl peroxide and cyclohexane peroxide.

Optional Chain Transfer Agents

Optionally, the composition also includes a chain transfer agent to control the molecular weight of the polymerized compositions. Chain transfer agents are materials that regulate free radical polymerization and are generally known in the art. Suitable chain transfer agents include halogenated hydrocarbons such as carbon tetrabromide; sulfur compounds such as lauryl mercaptan, butyl mercaptan, ethanethiol, isooctylthioglycolate (IOTG), 2-ethylhexyl thioglycolate, 2-ethylhexyl mercaptopropionate, 2-mercaptoimidazole, and 2-mercaptoethyl ether and mixtures thereof.

The amount of chain transfer agent that is useful depends upon the desired molecular weight and the type of chain transfer agent. The chain transfer agent is typically used in amounts from about 0.001 part to about 10 parts by weight per 100 parts of total monomer, and preferably from about Q.01 part to about 0.5 part, and most preferably from about 0.02 part to about 0.3 part. ps Water Soluble Salt Depending upon the use of the pressure sensitive adhesive of the present invention, various biocompatible and/or therapeutic and/or materials that provide ionic conductivity can be included in the adhesive.

For example, adhesives of the present invention can be used as conductive adhesive in a biomedical electrode with the addition of an ionically-conductive material to the adhesive. Nonlimiting examples of these materials include ionic salts dissolved in the adhesive to provide ionic conductivity and can include magnesium acetate, magnesium sulfate, sodium acetate, sodium chloride, sodium citrate, and preferably potassium chloride to enhance ionic conductivity of the pressure sensitive adhesive.

When present for ionically conductive biomedical electrodes and iontophoretic pharmaceutical delivery devices, the amounts of these ionic salts present in adhesives of the present invention are relatively small, from about 1 to 3 parts by weight.

Surfactant

Nonionic surfactants employed in the present invention can be copolymerizable with the monomers present or non-copolymerizable. The amounts of surfactant can range from about 10 to about 20 parts by weight.

1. Nonionic Surfactants

The nonionic surfactants are usually condensation products of an organic aliphatic or alkylaromatic hydrophobic compound and an alkylene oxide, such as ethylene oxide, which is hydrophilic. The length of the ethylene oxide chain of the condensation product can be adjusted to achieve the desired balance between the hydrophobic and hydrophilic elements (Hydrophilic-Lipophilic Balance or HLB). The HLB of a surfactant is an expression of the balance of the size and strength of the hydrophilic (water-loving or polar) and the lipophilic (oil-loving or non-polar) groups of the surfactant. The useful HLB of nonionic surfactants for the present invention is from about 6 to about 19, preferably from about 9 to about 18, and most preferably from about 10 to about 16. Useful nonionic surfactants include those selected from the group consisting of non(co)polymerizable nonionic surfactants, ethylenically-unsaturated copolymerizable nonionic surfactants, and mixtures thereof.

1.a. Non(co)polymerizable Nonionic Surfactants

Particularly suitable nonreactive nonionic surfactants include but are not limited to those selected from the group consisting of the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles, most preferably about 5 to about 20 moles of ethylene oxide to achieve the above defined HLB. Examples of such nonionic ethoxylated fatty alcohol surfactants are the Tergitol™ 15-S series from Union Carbide and Brij™ surfactants from ICI. Tergitol™ 15-S Surfactants include $C_{11}$–$C_{15}$ secondary alcohol polyethyleneglycol ethers. Brij™ 97 Surfactant is Polyoxyethylene(10) oleyl ether; Brij™ 58 Surfactant is Polyoxyethylene(20) cetyl ether; and Brij™ 76 Surfactant is Polyoxyethylene(10) stearyl ether.

Other suitable nonreactive nonionic surfactants include but are not limited to those selected from the group consisting of the polyethylene oxide condensates of one mole of alkyl phenol containing from about 6 to 12 carbon atoms in a straight or branched chain configuration, with about 3 to about 100 moles, preferably about 5 to about 40 moles, most preferably about 5 to about 20 moles of ethylene oxide to achieve the above defined HLB. Examples of nonreactive nonionic surfactants are the Igepal™ CO and CA series from Rhone-Poulenc. Igepal™ CO surfactants include nonylphenoxy poly(ethyleneoxy) ethanols. Igepal™ CA surfactants include octylphenoxy poly(ethyleneoxy) ethanols.

Another group of usable nonreactive nonionic surfactants include but are not limited to those selected from the group consisting of block copolymers of ethylene oxide and propylene oxide or butylene oxide with HLB values of about 6 to about 19, preferably about 9 to about 18, and most preferably about 10 to about 16. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers.

Still other satisfactory nonreactive nonionic surfactants include but are not limited to those selected from the group consisting of sorbitan fatty acid esters, polyoxyethylene sorbitan fatty acid esters and polyoxyethylene stearates having HLBs of about 6 to about 19, preferably about 9 to about 18, and most preferably about 10 to about 16. Examples of such fatty acid ester nonionic surfactants are the Span™, Tween™, and Myj™ surfactants from ICI. Span™ surfactants include $C_{12}$–$C_{18}$ sorbitan monoesters. Tween™ surfactants inlcude poly(ethylene oxide) $C_{12}$–$C_{18}$ sorbitan monoesters. Myj™ surfactants include poly (ethylene oxide) stearates.

1.b. Ethylenically-Unsaturated Copolymerizable Nonionic Surfactants

Suitable nonionic surfactants for incorporation in the microemulsions of this invention are ethylenically-unsaturated copolymerizable nonionic surfactants including but not limited to those selected from the group consisting of those falling within the general formula:

$$R-O-(R'O)_m-(EO)_{(n-1)}-CH_2CH_2OH$$

where R is selected from the group consisting of (about $C_2$ to about $C_{18}$) alkenyl, acrylyl (about $C_1$ to about $C_{10}$) alkyl, methacrylyl (about $C_1$ to about $C_{10}$) alkyl, vinylphenyl and vinylphenylene (about $C_1$ to about $C_6$) alkyl; R'O is selected from the group consisting of bivalent alkyleneoxy groups derived from epoxy compounds having more than two carbon atoms, preferably three or four carbon atoms, such as those selected from the group consisting of propylene oxide, butylene oxide, etc. and combinations thereof; E is a bivalent ethylene radical; m represents an integer of about 5 to about 100; n represents an integer of about 5 to about 100; the ratio of m and n being from about 20:1 to about 1:20. Varying the ratio of m and n will vary the HLB of the polymerizable surfactant. The required HLB for the nonionic surfactant(s) of the present invention is from about 6 to about 19, preferably from about 9 to about 18, and most preferably from about 10 to about 16. Examples of such copolymerizable nonionic surfactants are the alkylene polyalkoxy ethanol surfactants available from PPG Industries under the tradenames Mazon BSN™ 185, 186 and 187. Mazon BSN™ surfactants include alkylene polyalkoxy ethanol.

Other surfactants such as cationic and anionic surfactants can be used, as disclosed generally in U.S. Pat. No. 5,670, 557 (Dietz et al.), the disclosure of which is incorporated by reference herein.

Amine Functional Polymer

Nonlimiting examples of amine functional polymers include poly(vinyl amines), poly(allyl amines), poly (alkylene amines), poly(ethylenimine)("PEI") and alkylated versions thereof, poly(vinyl pyridines), poly(vinyl pyrroles), poly(N-vinyl lactams), and homopolymers or copolymers from monomers such as those of Formula (II):

Formula (II)

wherein
a is 0 or 1;
R is selected from H— and $CH_3$—,
X is selected from —O— and —NH—;
Y is a divalent linking group, preferably comprising about 1 to about 5 carbon atoms for ease of availability; and
Am is a amine fragment, primary, secondary or tertiary, of the Formula III:

Formula III wherein $R^1$ and $R^2$ are selected from H, alkyl, aryl, cycloalkyl, and arenyl groups. $R^1$ and $R^2$ in the above group may also form a heterocycle. Alternatively, Am can be pyridinyl or imidazolyl, substituted or unsubstituted. In all embodiments, Y, $R^1$, and $R^2$ may also comprise heteroatoms, such as O, S, N, etc.

Exemplary basic monomers include N,N-dimethylaminopropyl methacrylamide (DMAPMAm); N,N-diethylaminopropyl methacrylamide (DEAPMAm); N,N-dimethylaminoethyl acrylate (DMAEA); N,N-diethylaminoethyl acrylate (DEAEA); N,N-dimethylaminopropyl acrylate (DMAPA); N,N-diethylaminopropyl acrylate (DEAPA); N,N-dimethylaminoethyl methacrylate (DMAEMA); N,N-diethylaminoethyl methacrylate (DEAEMA); N,N-dimethylaminoethyl acrylamide (DMAEAm); N,N-dimethylaminoethyl methacrylamide (DMAEMAm); N,N-diethylaminoethyl acrylamide (DEAEAm); N,N-diethylaminoethyl methacrylamide (DEAEMAm); N,N-dimethylaminoethyl vinyl ether (DMAEVE); N,N-diethylaminoethyl vinyl ether (DEAEVE); and mixtures thereof. Other useful basic monomers include vinylpyridine, vinylimidazole, tertiary amino-functionalized styrene (e.g., 4-(N,N-dimethylamino)-styrene (DMAS), 4-(N,N-diethylamino)-styrene (DEAS)), and mixtures thereof.

Homopolymers can be made according to techniques known to those skilled in the art, including without limitation, cationic, ring-opening, and free radical polymerization.

The method of polymerization of these basic copolymers is disclosed in copending, coassigned, U.S. patent application Ser. No. 09/025,607 (Stark et al.), the disclosure of which is incorporated herein by reference. A "basic copolymer" is a polymer that is derived from at least one basic monomer and at least one non-basic copolymerizable monomer (i.e., a monomer that can not be titrated with an acid). In a preferred embodiment, at least one copolymerizable monomer is a (meth)acrylate monomer (e.g., an alkyl (meth) acrylate monomer). The basic copolymer may optionally be derived from other copolymerizable monomers, such as vinyl monomers and acidic monomers, as long as the copolymer can still be titrated with an acid. Thus, it is preferred that more basic monomers are utilized to prepare the basic copolymers than are acidic monomers. Most preferably, however, in order to efficiently impart cohesive strength to the adhesive, essentially no acidic monomers (i.e., the copolymerizable monomers include about 5 wt. % or less of acidic monomers, but most preferably, the copolymerizable monomers are free of acidic monomers) are utilized to prepare basic copolymers of the present invention.

When the basic polymer is a copolymer, the ratio of basic monomers to non-basic copolymerizable monomers utilized varies depending on desired properties of the resulting hot-melt adhesive. The properties of the hot-melt adhesive can also be adjusted by varying the amount of the basic copolymer in the blend.

Generally, as the proportion of basic monomers used in preparing the basic copolymer increases, cohesive strength of the resulting adhesive increases. The proportion of basic monomers is usually adjusted depending on the proportion of basic copolymer present in the blends of the present invention.

Of these polymers, PEI is presently preferred due to its commercial availability and its low cost.

The amine functional polymer can be added in an amount of between about 0.5 and about 10 parts by weight. Preferably, the amount is between 1 and 5 parts by weight.

Advantageously, increased cohesive strength can be achieved without an additional curing step. However, other types of curing (i.e., thermal, ultraviolet or electron beam radiation) can also be used in conjunction with the present hot-melt adhesives. Generally, however, they are not necessary.

Other advantages of utilizing blends of the present invention include the ability to provide thick adhesive coatings with sufficient crosslinking throughout the thickness. Previously, this was often difficult and problematic when utilizing photoactivated crosslinking agents because it was difficult for UV-radiation to penetrate the entire thickness of certain adhesive coatings.

Adhesive Preparation

The conductive pressure sensitive adhesive compositions can be used to make a coatable thermoplastic hot melt pressure sensitive adhesive by introducing the base copolymer, humectant/hydrophilic plasticizer, water, salt, crosslinker and other optional additives into a vessel in which the mixture is compounded and melted.

There are two basic steps to adhesive preparation: polymerization of monomers and blending of amine functional polymers and other components. There are two known methods using these two basic steps, described in the Summary of the Invention above. The difference between the two methods is the inclusion of some surfactant and water in the polymerization vessel for one of the methods vs. waiting until the mixing to add these ingredients. The inclusion of some surfactant allows better mixing of the monomers and management of resulting polymer molecular weight, and the water provides a heat sink for the exotherm of polymerization and reduces viscosity of the resulting polymer for subsequent mixing. This inclusion method is the preferred method.

Polymerization Methods

The polymers herein can be prepared by any conventional free radical polymerization method, including solution, radiation, and bulk processes.

In one solution polymerization method, the monomers, water, plasticizer, and some of the surfactant, optionally along with a suitable inert organic solvent, are charged into a four-neck reaction vessel that is equipped with a stirrer, a thermometer, a condenser, an addition funnel, and a thermowatch. A concentrated thermal free radical initiator solution is added to the addition funnel. The whole reaction vessel, addition funnel, and their contents are then purged with nitrogen to create an inert atmosphere. Once purged, the solution within the vessel is heated to an appropriate temperature to activate the free radical initiator to be added, the initiator is added, and the mixture is stirred during the course of the reaction. A 98% to 99% conversion should be obtained in about 20 hours. If the optional solvent is used, it must be removed before coating of the adhesive.

Another polymerization method is ultraviolet (UV) radiation-initiated photopolymerization of the monomer/plasticizer mixture. After pre-polymerization to a coatable viscosity, the mixture, along with a suitable photoinitiator and plasticizer, is coated onto a flexible carrier web and polymerized in a sufficiently inert (i.e., essentially oxygen free) atmosphere (e.g., a nitrogen atmosphere). A sufficiently inert atmosphere can be achieved by covering a layer of the photoactive coating with a plastic film that is substantially transparent to ultraviolet radiation and irradiating through the plastic film in air using low intensity, fluorescent-type ultraviolet lamps that generally give a total radiation dose of about 500 milliJoules/cm$^2$.

Bulk polymerization methods, such as the continuous free radical polymerization method described by Kotnour et al. in U.S. Pat. Nos. 4,619,979 and 4,843,134; the essentially adiabatic polymerization methods using a batch reactor described by Ellis in U.S. Pat. No. 5,637,646; and, the methods described for polymerizing packaged pre-adhesive compositions described by Hamer et al. in U.S. Pat. No. 5,804,610 can also be utilized to prepare the polymers. All of these patents are incorporated by reference herein.

Blending

Blending of the polymers is done by any method that results in a substantially homogenous distribution of the acidic (meth)acrylate polymer and the basic amine functional polymer. The polymers can be blended using several methods. For example, the polymers can be blended by melt blending, solvent blending, or any suitable physical means.

For example, the polymers can be melt blended by a method as described by Guerin et al. in U.S. Pat. No. 4,152,189, the disclosure of which is incorporated by reference herein. That is, all solvent (if used) is removed from each polymer by heating to a temperature of about 150° C. to about 175° C. at a pressure of about 5 Torr to about 10 Torr. Then, the polymers are weighed into a vessel in the desired proportions. The blend is then formed by heating the contents of the vessel to about 175° C., while stirring.

Although melt blending is preferred, the adhesive blends of the present invention can also be processed using solvent blending. The acidic and basic polymers should be substantially soluble in the solvents used.

Physical blending devices that provide dispersive mixing, distributive mixing, or a combination of dispersive and distributive mixing are useful in preparing homogenous blends. Both batch and continuous methods of physical blending can be used. Examples of batch methods include BRABENDER (using a BRABENDER PREP CENTER, available from C. W. Brabender Instruments, Inc.; South Hackensack, N.J.) or BANBURY internal mixing and roll milling (using equipment available from FARREL COMPANY; Ansonia, Conn.). Examples of continuous methods include single screw extruding, twin screw extruding, disk extruding, reciprocating single screw extruding, and pin barrel single screw extruding. The continuous methods can include utilizing both distributive elements, such as cavity transfer elements (e.g., CTM, available from RAPRA Technology, Ltd.; Shrewsbury, England) and pin mixing elements, static mixing elements and dispersive elements (e.g., MADDOCK mixing elements or SAXTON mixing elements as described in "Mixing in Single-Screw Extruders," *Mixing in Polymer Processing*, edited by Chris Rauwendaal (Marcel Dekker Inc.: New York (1991), pp. 129, 176–177, and 185–186).

Coating

The resulting hot melt pressure sensitive adhesive can be used to form a pressure sensitive adhesive sheet by coating the melted pressure sensitive adhesive onto a sheet material or another suitable substrate. The sheet material is preferably selected from a tape backing or a transfer liner. Preferably, the conductive pressure sensitive adhesives are hot melt coated from a hot melt coater at a temperature sufficient to melt and thoroughly mix the components, which is then coated onto a substrate. This step can be done conveniently in a heated extruder, bulk tank melter, melt-on-demand equipment, or a hand-held hot melt adhesive gun. Advantageously, the properties of the compounded pressure-sensitive adhesive can be adjusted by simply adjusting the metering ratio of the base polymer to other additives The coatable conductive hot melt pressure sensitive adhesive can be delivered out of a film die and subsequently coated by contacting the drawn adhesive with a moving plastic web or other suitable substrate. A related coating method involves extruding the coatable plasticized thermoplastic hot melt pressure sensitive adhesive and a coextruded backing material from a film die and cooling the layered product to form a pressure sensitive adhesive tape. Other forming methods involve directly contacting the coatable conductive hot melt pressure sensitive adhesive to a rapidly moving plastic web or other suitable preformed substrate. Using this method, the conductive pressure sensitive adhesive blend is applied to the moving preformed web using a die having flexible die lips, such as a rotary rod die. After forming by any of these continuous methods, the pressure sensitive adhesive films or layers can be solidified by quenching using both direct methods (e.g., chill rolls or water baths) and indirect methods (e.g., air or gas impingement).

The steps can be done in-line or the steps can be performed individually at separate times and sites.

Biomedical Electrodes

Biomedical electrodes employing polymerized hot melt PSA's of the present invention having electrolyte contained therein are useful for diagnostic, (including monitoring), and therapeutic purposes. In its most basic form, a biomedical electrode comprises a conductive medium contacting mammalian skin and a means for electrical communication interacting between the conductive medium and electrical diagnostic, therapeutic, or electrosurgical equipment.

Figure 1:
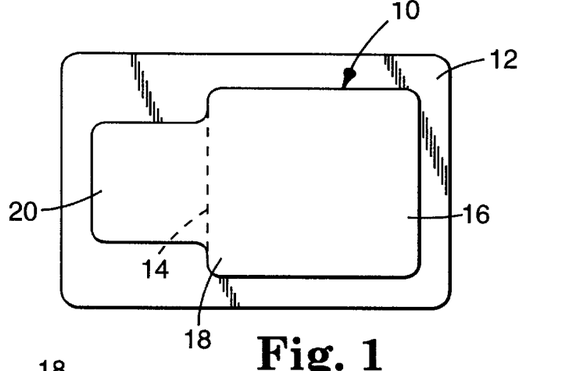
FIG. 1 is a top plan view of a biomedical electrode containing a hot melt PSA of the present invention, used for diagnosis or monitoring of heart conditions of a mammalian patient.
Figure 2:
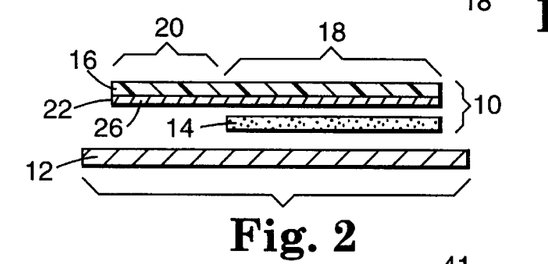
FIG. 2 is a cross-sectional view of the biomedical electrode of FIG. 1.

FIGS. 1 and 2 show either a disposable diagnostic electrocardiogram (ECG or EKG) or a transcutaneous electrical nerve stimulation (TENS) electrode 10 on a release liner 12. Electrode 10 includes a field 14 of a biocompatible and adhesive conductive medium for contacting mammalian skin of a patient upon removal of protective release liner 12. Electrode 10 includes means for electrical communication 16 comprising a conductor member having a conductive interface portion 18 contacting field 14 of conductive medium and a tab portion 20 extending beyond field 14 of conductive medium for mechanical and electrical contact with electrical instrumentation (not shown). Means 16 for electrical communication includes a conductive layer 26 coated on at least the side 22 contacting field 14 of conductive medium.

It is foreseen that a typical conductor member 16 will comprise a strip of material having a thickness of about 0.05–0.2 millimeters, such as polyester film and have a coating 26 on side 22 of silver/silver chloride of about 2.5–12 micrometers, and preferably about 5 micrometers thick thereon. Presently preferred for conductor member 16 are polyester films commercially available as "Scotchpar" commercially available from Minnesota Mining and Manufacturing Company of St. Paul, Minn. or "Melinex" 505–300, 329, or 339 film from ICI Americas of Hopewell, Va. commercially available as "Mellinex" 505–300, 329, or 339 film from ICI Americas of Hopewell, Va. coated with a silver/silver chloride ink commercially available as "R-300" ink from Ercon, Inc. of Waltham, Mass. A TENS conductor member 16 can be made of a nonwoven web, such as a web of polyester/cellulose fibers commercially available as "Manniweb" web from Lydall, Inc. of Troy, N.Y. and have a carbon ink layer 26 commercially available as "SS24363" ink from Acheson Colloids Company of Port Huron, Mich. on side 22 thereof. To enhance mechanical contact between an electrode clip (not shown) and conductor member 16, an adhesively-backed polyethylene tape can be applied to tab portion 20 on the side opposite side 22 having the conductive coating 26. A surgical tape commercially available from 3M Company as "Blenderm" tape can be employed for this purpose.

Alternatively, conductor member can be a multi-layered construction of a nonconductive, flexible polymeric film having a sulfur-reactive surface, a metallic layer deposited on and interacting with the surface and an optional metallic halide layer, according to the disclosure of U.S. Pat. No. 5,506,059 (Robbins et al.), the disclosure of which is incorporated by reference herein. The conductive interface portion 18 of member 16 comprises a metallic layer deposited on an sulfur-reactive surface on at least the side of polymeric film substrate facing field 14 of the polymerized hot melt PSA and the optional metallic halide layer coated on the metallic layer and contacting field 14. Because depolarizing is not needed for the mechanical and electrical contact with electrical equipment, optional metallic halide layer does not need to extend to tab portion 20.

Alternatively, conductor member 16 can be a multi-layered construction of a nonconductive, flexible polymeric film, an electrically conductive layer, and a thin, conformable depolarizing layer of inorganic oxide, preferably manganese dioxide. Alternatively, conductor member 16 is a multi-layered construction of film with electrically conductive and depolarizing layers blended together. Both of these alternative embodiments can be constructed according to the disclosure of U.S. Pat. No. 5,505,200 (Takaki), the disclosure of which is incorporated by reference herein. The conductive interface portion of member comprises an electrically conductive layer coated on at least the side of polymeric film facing field 14 of polymerized hot melt PSA and the thin, depolarizing layer coated on the electrically conductive layer and contacting field 14. Because depolarizing is not needed for the mechanical and electrical contact with electrical equipment, depolarizing layer not extend to tab portion 20.

Non-limiting examples of biomedical electrodes which can use polymerized hot melt PSA's of the present invention, either as conductive or non-conductive adhesive fields include electrodes disclosed in U.S. Pat. Nos. 4,524,087; 4,539,996; 4,554,924; 4,848,353 (all Engel); U.S. Pat. No. 4,846,185 (Carim); U.S. Pat. No. 4,771,713 (Roberts); U.S. Pat. No. 4,715,382 (Strand); U.S. Pat. No. 5,012,810 (Strand et al.); and U.S. Pat. Nos. 5,133,356 (Bryan et al.), 5,489,624 (Kantner), the disclosures of which are incorporated by reference herein.

In those electrodes that also employ border areas of a non-conductive biocompatible pressure sensitive adhesive, such border areas become optional with the use of polymerized hot melt PSA's of the present invention. Desirably, such border areas can be eliminated because it is no longer necessary.

In some instances, the means for electrical communication can be an electrically conductive tab extending from the periphery of the biomedical electrodes such as that seen in U.S. Pat. No. 4,848,353 or can be a conductor member extending through a slit or seam in an insulating backing member, such as that seen in U.S. Pat. No. 5,012,810. Otherwise, the means for electrical communication can be an eyelet or other snap-type connector such as that disclosed in U.S. Pat. No. 4,846,185. Further, the means for electrical communication can be a lead wire such as that seen in U.S. Pat. No. 4,771,783. Regardless of the type of means for electrical communication employed, a polymerized hot melt PSA of the present invention, containing an electrolyte, can reside as a field of conductive adhesive on a biomedical electrode for diagnostic (including monitoring), therapeutic, or electrosurgical purposes.

Another type of diagnostic procedure which can employ a biomedical electrode of the present invention is the longer term monitoring of electrical wave patterns of the heart of a patient to detect patterns of abnormality. A preferred biomedical electrode structure is disclosed in U.S. Pat. No. 5,012,810 (Strand et al.) which is incorporated by reference. The polymerized hot melt PSA of the present invention can be used as the ionically conductive medium in any of the embodiments shown therein. Preferably, the polymerized hot melt PSA of the present invention is used as the field of conductive adhesive in the biomedical electrode of the embodiment shown in FIGS. 2, 3, and 4 of U.S. Pat. No. 5,012,810.

Figure 3:
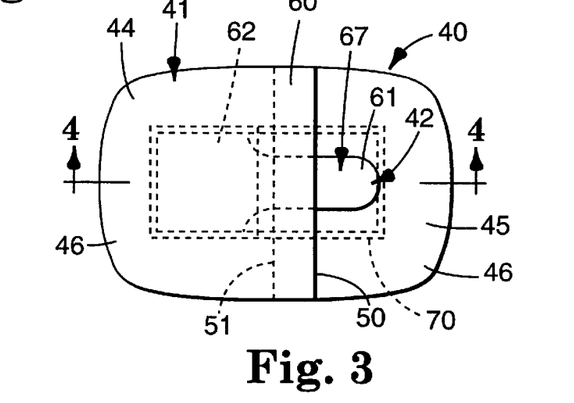
FIG. 3 is a top plan view of a monitoring biomedical electrode containing a polymerized hot melt PSA of the present invention, used for longer term diagnosis or monitoring of heart conditions.
Figure 4:
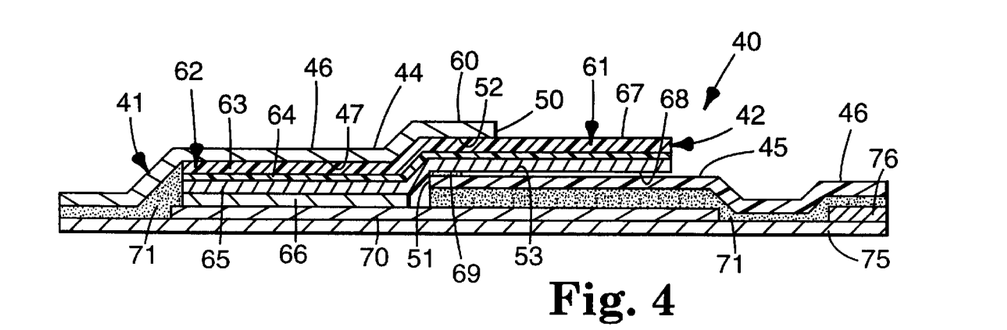
FIG. 4 is a cross-sectional view of the monitoring biomedical electrode of FIG. 3.

FIGS. 3 and 4 substantially correspond to FIGS. 2 and 3, respectively, of U.S. Pat. No. 5,012,810. Electrode 40 includes an insulator construction 41, and a conductor member 42.

The insulator construction 41 includes first and second sections 44 and 45 which, together, define opposite sides 46 and 47 of the insulator construction 41. As seen in FIG. 3, each section 44 and 45 includes an elongate edge portion 50 and 51, respectively. The edge portions 50 and 51 each include a border portion 52 and 53, respectively, which comprise a peripheral portion of each section 44 and 45, respectively, and extending along edges 50 and 51, respectively. In that manner, sections 44 and 45 are oriented to extend substantially parallel to one another, with edge portions 50 and 51 overlapping one another such that border portions 52 and 53 overlap. A seam 60 is created between edge portions 50 and 51. "Substantially parallel" does not mean that the sections 44 and 45 are necessarily precisely parallel. They may be out of precise coplanar alignment due, for example, to the thickness of the conductor member 42.

Conductor member 42 is substantially similar to biomedical electrical conductor 16 described above, having a tab portion 61 corresponding to tab portion 20 described above and a pad portion 62 corresponding to conductive interface portion 18 described above. Like biomedical electrical conductor member 16, conductor member 42 can be any of the embodiments disclosed above. In this embodiment, conductor member 42 is a multi-layered construction of a nonconductive, flexible organic polymer substrate 63 having an organosulfur surface 64, a metallic layer 65 adhered thereto, and, optionally, a metallic halide layer 66, produced according to the disclosure of Robbins et al. described above.

The pad portion 62 of member 42 comprises the portion of the metallic film facing field 70 of conductive adhesive, optionally with metallic halide layer 66 contacting field 70. Because depolarizing is not needed for the mechanical and electrical contact with electrical equipment, metallic halide layer 66 need not extend to tab portion 61. Optionally, an adhesively-backed polyethylene tape can be applied to tab portion 61 in the same manner as that for the embodiment of FIGS. 1 and 2 in order to enhance mechanical contact.

In general, electrode 40 is constructed such that tab portion 61 of conductor member 42 projects through seam 60 and over a portion of surface or side 46. As a result, as seen in FIGS. 3 and 4 pad portion 62 of conductor member 42 is positioned on one side 47 of insulator construction 41, and the tab portion 61 of conductor member 42 is positioned on an opposite side 46 of insulator construction 41. It will be understood that except where tab portion 61 extends through seam 60, the seam may be sealed by means of an adhesive or the like.

As seen in FIG. 4, lower surface 68 of tab portion 61 is shown adhered in position to section 45, by means of double-stick tape strip 69. That is, adhesion in FIG. 1 between the tab portion 61 and section 45 is by means of adhesive 69 underneath tab portion 61, rather than on top as shown in FIG. 3.

In FIG. 4, a field 70 of conductive adhesive of polymerized hot melt PSA of the present invention is shown positioned generally underneath conductive member 42. Optionally, field 70 of conductive adhesive will be surrounded by a field 71 of biocompatible skin adhesive also applied to insulator construction 41 the side thereof having pad portion 62 thereon. However, because of the hydrophobic pressure sensitive adhesive bulk properties of the polymerized hot melt PSA of the present invention, field 71 can be eliminated or can be also the polymerized hot melt PSA of the present invention.

In FIG. 4, a layer of release liner 75 is shown positioned against that side of electrode 40 which has optional skin adhesive 71, conductive adhesive 70 and pad portion 62 thereon. Optionally as shown in FIG. 4, a spacer 76 or tab 76 can be positioned between release liner 75 and a portion of insulator construction 41, to facilitate the separation.

A variety of release liners 75 can be utilized; for example, a liner comprising a polymer such as a polyester or polypropylene material, coated with a silicone release type coating which is readily separable from the skin adhesive and conductive adhesive.

A variety of materials can be utilized to form the sections 44 and 45 of the insulator construction 41. In general, a flexible material is preferred which will be comfortable to the user, and is relatively strong and thin. Preferred materials are polymer foams, especially polyethylene foams, non-woven pads, especially polyester non-wovens, various types of paper, and transparent films. Nonlimiting examples of transparent films include polyester film such as a polyester film commercially available as "Melinex" polyester film from ICI Americas, Hopewell, Va. having a thickness of 0.05 mm and a surgical tape commercially available from 3M Company as "Transpore" unembossed tape.

The most preferred materials are non-woven pads made from melt blown polyurethane fibre, which exhibit exceptional flexibility, stretch recovery and breathability. Melt blown polyurethane materials usable in insulator construction 41 in electrodes according to the present invention are generally described in European Patent Publication 0 341 875 (Meyer) and corresponding U.S. Pat. No. 5,230,701 (Meyer et al.), incorporated herein by reference.

Optionally the insulator construction has a skin adhesive on its surface contacting the remainder of the electrode 40.

Preferred web materials (melt blown polyurethanes) for use in insulator construction 41 have a web basis weight of about 60–140 g/m2 (preferably about 120 g/m2). Such materials have an appropriate tensile strength and moisture vapor transmission rate. A preferred moisture vapor transmission rate is about 500–3000 grams water/$m^2$/24 hours (preferably 500–1500 grams water/m2/24 hours) when tested according to ASTM E96-80 at 21° C. and 50% relative humidity. An advantage to such materials is that webs formed from them can be made which exhibit good elasticity and stretch recovery. This means that the electrode can stretch well, in all directions, with movement of the subject, without loss of electrode integrity and/or failure of the seal provided by the skin adhesive. Material with a stretch recovery of at least about 85%, in all directions, after stretch of 50% is preferred.

It will be understood that a variety of dimensions can be utilized for the biomedical electrode disclosed herein. Generally an insulator construction of about 3.5–4.5 cm by 5.5.10 cm will be quite suitable for typical foreseen applications. A thickness of about 200 to 600 mm provides for adequate strength and a desired low relief or profile, in typical applications.

It will also be understood that a variety of materials can be utilized as the skin adhesive, if polymerized hot melt PSA is not employed or if the field 71 is not eliminated. Typically, acrylate ester adhesives will be preferred. Acrylate ester copolymer adhesives are particularly preferred. Such material are generally described in U.S. Pat. Nos. 2,973,826; Re. 24,906; Re. 33,353; 3,389,827; 4,112,213; 4,310,509; 4,323, 557; 4,732,808; 4,917,928; 4,917,929; and European Patent Publication 0 051 935, all incorporated herein by reference.

In particular, an adhesive copolymer having from about 95 to about 97 weight percent isooctyl acrylate and from about 5 to about 3 percent acrylamide and having an inherent viscosity of 1.1–1.25 dl/g is presently preferred.

Adhesive useful as for adhesive 69 can be any of the acrylate ester adhesives described above in double stick tape form. A presently preferred adhesive is the same adhesive as presently preferred for the skin adhesive except having an inherent viscosity of about 1.3–1.45 dl/g. For the field 70 of conductive adhesive, conductive adhesives such as those described above as useful for field 14 of conductive medium are preferred. It will be understood that the dimensions of the various layers, and their conformation during association, are shown somewhat exaggerated in FIG. 4, to facilitate an understanding of the construction. In general, an overall substantially flat appearance with only a very minor "s" type bend in the conductive member 42 is accommodated by the arrangement, despite the multi-layered construction of member 42.

Figure 5:
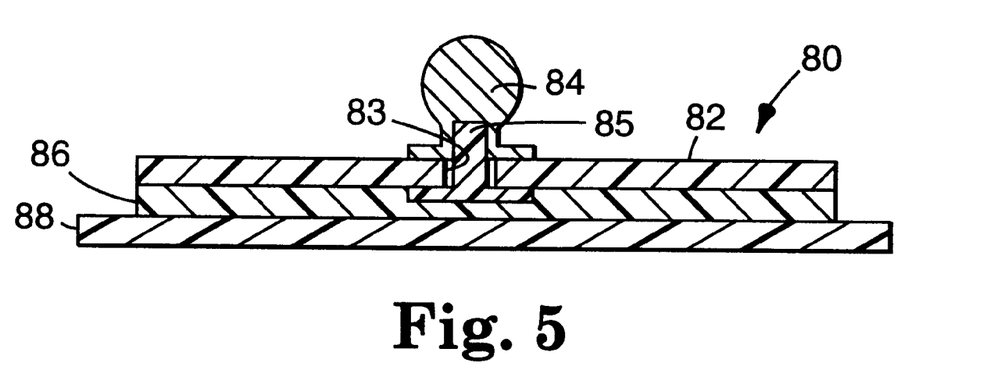
FIG. 5 is a cross-sectional view of another monitoring biomedical electrode containing a polymerized hot melt PSA of the present invention and a stud connector.

Another biomedical electrode construction is shown in FIG. 5 in cross-section. Electrode 80 has a nonconductive backing 82 having an opening 83 covered by snap 84 though which stud or eyelet 85 protrudes. The snap 84 is secured to eyelet 85 to provide a point of electrical connection to electrical instrumentation. Covering eyelet 84 and backing 82 is a field 86 of the polymerized hot melt PSA of the present invention. A release liner 88 protects the PSA field 86 prior to use. Backing 82 can be made of the same or similar materials as insulator construction 41 or can be a polyethylene/polypropylene blended film commercially available from Milliken. Eyelet 85 can be a plastic, metallic plated eyelet (such as an ABS plastic eyelet silver-plated and chlorided and commercially available from Micron Products of Fitchburg, Mass.). Snap 84 can be a metallic snap (such as stainless steel eyelet No. 304 commercially available from Eyelets for Industry of Thomason, Conn.). Electrode 80 is particularly preferred because the polymerized hot melt PSA of the present invention can serve both as the biocompatible skin adhesive and as the ionically conductive medium in the electrode 80. By comparison, a monitoring electrode that requires a skirt of biocompatible skin adhesive to surround a nonadhesive but ionically conductive gel pad, such as a Red Dot™ brand electrode commercially available from Minnesota Mining and Manufacturing Company is a more complicated construction.

Other examples of biomedical electrodes which can use the present invention as a conductive adhesive include electrodes disclosed in U.S. Pat. Nos. 4,527,087; 4,539,996; 4,554,924; 4,848,353 (all Engel); U.S. Pat. No. 4,846,185 (Carim); U.S. Pat. No. 4,771,713 (Roberts); U.S. Pat. No. 4,715,382 (Strand); U.S. Pat. No. 5,133,356 (Bryan et al.), the disclosures of which are incorporated by reference herein. Methods of making such electrodes are disclosed in such patents, except that polymerized hot melt PSA of the present invention can be substituted for the field of conductive adhesive and optionally also the field of skin adhesive disclosed in such patents. Among these various electrode constructions is an electrode construction particularly preferred as that shown in FIGS. 4 and 5 of U.S. Pat. No. 4,848,353 (Engel) in which the electrically conductive adhesive 36 is replaced by the polymerized hot melt PSA of the present invention, and in which the biocompatible PSA 32 is optionally eliminated or optionally replaced by the polymerized hot melt PSA of the present invention. When used for diagnostic EKG procedures, electrodes shown in FIGS. 5 and 6 or those electrodes shown in U.S. Pat. No. 4,539,996 are preferred. When used for monitoring electrocardiogram (ECG) procedures, electrodes shown in FIGS. 7 and 8 and those disclosed in U.S. Pat. Nos. 4,539,996, 4,848,353, 5,012,810 and 5,133,356 are preferred.

In some instances, the biomedical electrical conductor can be an electrically conductive tab extending from the periphery of the biomedical electrodes such as that seen in U.S. Pat. No. 4,848,353 or can be a conductor member extending through a slit or seam in a insulating backing member, such as that seen in U.S. Pat. No. 5,012,810. Otherwise, the means for electrical communication can be an eyelet or other snap-type connector such as that disclosed in U.S. Pat. No. 4,846,185. Alternatively, an electrically conductive tab such as that seen in U.S. Pat. No. 5,012,810 can have an eyelet or other snap-type connector secured thereto.

Pharmaceutical Delivery Devices

Pharmaceutical delivery devices employing hydrophilic, pressure-sensitive adhesive compositions of the present invention, optionally having a topical, transdermal, or iontophoretic therapeutic agent and excipients, solvents, or penetration enhancing agents contained therein, are useful for delivery of pharmaceuticals or other active agents to or through mammalian skin.

Figure 6:
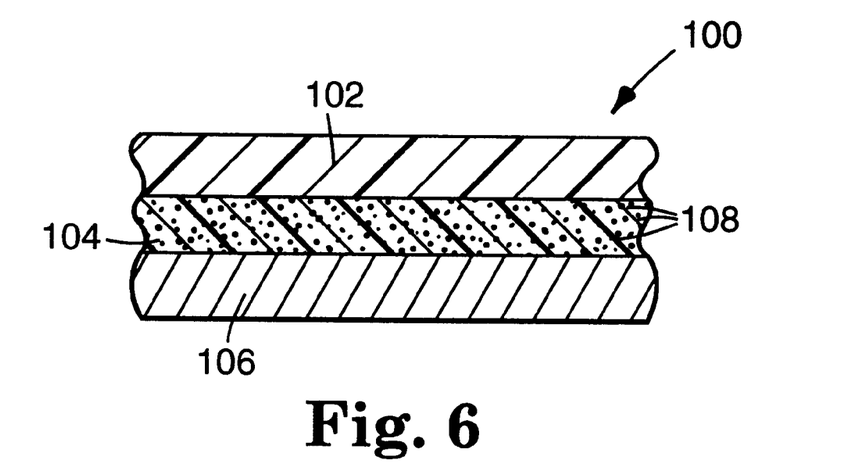
FIG. 6 is a sectional view of a pharmaceutical delivery device containing a polymerized hot melt PSA of the present invention.

FIG. 6 shows a sectional view of a transdermal or topical drug delivery device 100 having a backing layer 102, a layer 104 containing polymerized hot melt PSA of the present invention coated thereon and protected by a release liner 106. Other layers can be present between layer 102 and layer 104 to house pharmaceuticals or other therapeutic agents. Otherwise, as shown in FIG. 6, pharmaceutical and other agents 108 are dispersed in adhesive layer 104.

The backing layer 102 can be any backing material known to those skilled in the art and useful for drug delivery devices. Non-limiting examples of such backing materials are polyethylene, ethylene-vinyl acetate copolymer, polyethylene-aluminum-polyethylene composites, and "ScotchPakTm" brand backings commercially available from Minn. Mining and Manufacturing Company of St. Paul, Minn. (3M).

The release liner 106 can be any release liner material known to those skilled in the art. Non-limiting examples of such release liners commercially available include siliconized polyethylene terephthalate films commercially available from H. P. Smith Co. and fluoropolymer coated polyester films commercially available from 3M under the brand "ScotchPak™" release liners.

The therapeutic agent 108 can be any therapeutically active material known to those skilled in the art and approved for delivery topically to or transdermally or iontophoretically through the skin of a patient. Non-limiting examples of therapeutic agents useful in transdermal delivery devices are any active drug or salts of those drugs, used in topical or transdermal applications, or growth factors for use in enhancing wound healing. Other therapeutic agents identified as drugs or pharmacologically active agents are disclosed in U.S. Pat. Nos. 4,849,224 and 4,855,294, and PCT Patent Publication WO 89/07951.

Excipients or penetration enhancing agents are also known to those skilled in the art. Non-limiting examples of penetration enhancing agents include ethanol, methyl laurate, oleic acid, isopropyl myristate, and glycerol monolaurate. Other penetration enhancing agents known to those skilled in the art are disclosed in U.S. Pat. Nos. 4,849,224; and 4,855,294 and PCT Patent Publication WO 89/07951.

The method of manufacturing a transdermal delivery device depends on its construction.

The drug delivery device 100 shown in FIG. 6 can be prepared using the following general method. A solution is prepared by dissolving the therapeutic agent 108 and such optional excipients as are desired in a suitable solvent and mixed into the monomers prior to forming the composition, during the formation of the composition, or directly into the already formed composition. The resulting loaded adhesive composition is coated on the backing layer 102. A release liner 106 is applied to cover loaded adhesive layer 104.

Test Methods

Skin adhesion test

The Examples discussed below were laminated onto a polypropylene/polyethylene backing and then were cut into 1"×3" (2.54 cm by 7.6 cm) strips. The strips were applied on the backs of human subjects perpendicular to the backbone and rolled with a 2 kg roller to insure uniform application. The strips were removed promptly after application from the back using a mechanical pulling device termed an adhesion tester. This device consists of a motor driven screw drive which pulls a 11.4 kg test line to which is attached a metal clip which is 2.54 cm wide. The metal clip is attached to each strip at its 2.54 cm width during pulling testing. Strips were pulled in a plane parallel (180°) to the back and parallel to the long axis of the strip at a rate of 13–14 cm/min. The adhesion is reported in grams/inch (g/2.54 cm) and based on an average of values from initiation of peel to entire removal of the electrode.

Electrical test

Samples of the Examples discussed below were laminated onto an Ag/AgCl conducting polyester backing and then were cut into 1"×1" inch (2.5 cm by 2.5 cm) squares. Standard tests according to AAMI standards were run on an X-tratec-65A ECG Electrode Tester from Xtratec Company of Lenexa, Kan. The average AC impedance through a back-to-back (adhesive-to adhesive) electrode pair at 10 Hz. (According to the Association for the Advancement of Medical Instrumentation (AAMI), the impedance value should not exceeding 2000 ohms.) The Defibrillation Overload Recovery value for a back-to-back electrode pair was assessed, determining the value of polarization potential across the electrode pair and the rate of change of the recovery slope after several simulated defibrillations. (According to AAMI, the value should not exceeding −1 mV/sec on the fourth pulse.) The results were as follows:

Skin impedance test

Samples of the Examples discussed below were tested for skin impedance. Values for skin impedance were measured using a 4800A Vector Impedance Meter manufactured by Hewlett Packard of Palo Alto Calif. on human arms. Biomedical electrodes were placed on the panelists' arms and measured for alternating current impedance in kOhms at a frequency of 10 Hz. Biomedical electrodes (Red Dot.TM. Brand Model 2330 biomedical electrodes commercially available from 3M, St. Paul, Minn.) were used as the reference electrodes.

EXAMPLES

Example 1

Two solutions were prepared, an aqueous solution containing:

7.7 grams KCl, 84.3 grams deionized water, 51 grams glycerin, 70.2 grams acrylic acid (AA), and 11.2 grams beta carboxyethyl acrylate (CEA);

and a non-aqueous solution containing:

31.7 grams iso-octyl acrylate (IOA), 0.215 grams $CBr_4$, and 0.429 grams VAZO 64 thermal initiator (DuPont of Wilmington, Del.) The two solutions were mixed in a bottle, which was then placed in a laundrometry at 60° C. for 24 hours. The polymer was then compounded in a Brabender mixer with 0.68 grams PEI, at 60° C. to 75° C. for about 40 minutes. The final water percentage was calculated by weighing a piece of sample, then heating it at 90° C., then re-weighing the sample. The final composition in the sample is listed in Table 1.

Examples 2–5

Additional similar examples with variations were prepared. However, during compounding in the Brabender mixer with PEI, different quantities of the surfactant, Brij™ 97 Surfactant (Polyoxyethylene(10) oleyl ether from ICI) were included. The conditions in the mixer were still from 60° C. to 75° C. for about 40 minutes. The samples appeared to be colloid structured adhesives. The final compositions for example 2–5 are also listed in Table 1 below.

Examples 6 and 7

In example 6, a single solution was prepared containing:

53 grams IOA, 76.1 grams AA, 3 grams βCEA, 0.2 grams iso-octylthioglycolate (IOTG), 0.195 grams Irg 184, 20 grams glycerin, and 48 grams PEG400.

The solution appeared to be one clear phase. About 18 grams of above solution was added into a pouch made of ethylene vinyl acetate copolymer about 6% vinyl acetate. Ten pouches containing the same solution were placed in a water bath at 16° C. Polymerization was carried out with UV light having an intensity of 3.5 m $Watt/cm^2$; the residence time under the lights was 10 minutes.

After polymerization, the pouches were either opaque or clear, depending on the percentage of the glycerin/PEG400. The pouches were then compounded in the Brabender mixer with a solution consist of 15% w/w Brij 97, 2.35% PEI and 2% KCl water at 95° C. to 65° C. for about 1.5 hours. Again, the it appeared that a polymer colloid structured adhesive was generated.

In example 7, polymerization process was the similar to the example 6, except the chain transfer agent % was higher. The final component % were calculated and listed in Table 1 below.

Each of the compounded adhesive examples 1–7 was hot pressed at about 70° C. to form a film.

Example 8

A polymer was prepared using the method of Example 1 using the ingredients listed in Table 1 below. The polymer mixture was then pumped into an 18-mm twin screw extruder at 90° C. by a 1.22 cc/rev melt pump commercially available from Leistrich. Simultaneously, a solution of a surfactant mixed with a PEI as an ionic crosslinker was also pumped into the extruder by a liquid pump commercially available from Zenith. The extruder then pumped the blend polymer adhesive to a 15.25 cm wide web running at 3 m/min. through a 12.5 cm wide rotary die to coat an approximately 0.33 mm thick adhesive film. The adhesive film on the web was rapidly cooled down to room temperature.

The films made from example 1–8 were then tested for their adhesive and electrical properties. Three tests were performed according to the testing protocols discussed above and are shown in Table 2 below.

TABLE 1

| Example | IOA | AA | β-CEA | Glycerin | PEG | Brij 97 | PEI | $CBr_4$ | IOTG | Water | KCl |
|---|---|---|---|---|---|---|---|---|---|---|---|
| | | | | % of total weight | | | | | | | |
| 1 | 13.3 | 26.5 | 4.4 | 21.8 | 0 | 0.0 | 0.99 | 0.133 | 0 | 22.0 | 2.2 |
| 2 | 13.6 | 17.3 | 1.44 | 18.6 | 0 | 16.5 | 0.90 | 0.097 | 0 | 23.2 | 2.2 |
| 3 | 15.8 | 18.5 | 0.88 | 20.2 | 0 | 15.4 | 0.91 | 0.106 | 0 | 22.2 | 2.2 |
| 4 | 15.3 | 20.9 | 1.39 | 12.9 | 6.9 | 12.4 | 0.95 | 0 | 0.075 | 27.0 | 2.2 |

TABLE 1-continued

| Example | IOA | AA | β-CEA | Glycerin | PEG | Brij 97 | PEI | CBr$_4$ | IOTG | Water | KCl |
|---|---|---|---|---|---|---|---|---|---|---|---|
| 5 | 14.5 | 19.7 | 1.31 | 12.2 | 6.5 | 14.0 | 0.72 | 0 | 0.100 | 28.9 | 1.9 |
| 6 | 15.5 | 22.2 | 0.88 | 5.8 | 14.0 | 14.4 | 0.91 | 0 | 0.058 | 20.8 | 2.2 |
| 7 | 16.5 | 23.6 | 0.93 | 6.2 | 14.9 | 14.8 | 0.93 | 0 | 0.116 | 18.8 | 2.2 |
| 8 | 9.67 | 14.3 | 0.87 | 9.92 | 4.34 | 15 | 0.91 | 0 | 0.058 | 38.0 | 1.2 |

TABLE 2

| Examples | Skin adhesion Peel test average of 2–5 tests | | AC impedance | Defibrillation recovery | Skin impedance |
|---|---|---|---|---|---|
| | grams/(2.54 cm)$^2$ | Observed residue | ohms | mV/sec | kOhms |
| Example 1 | 30 | no residue | 48 | −0.5 | — |
| Example 2 | 220 | light residue | 156 | −0.7 | — |
| Example 3 | 100 | no residue | 201 | −0.6 | — |
| Example 4 | 114 | no residue | 50.5 | −0.3 | 207.9* |
| Example 5 | 72.5 | no residue | 65.0 | −0.5 | 218.2* |
| Example 6 | 161 | no residue | 143.5 | −0.4 | — |
| Example 7 | 110 | no residue | 227 | −0.5 | — |
| Example 8 | — | — | 30 | −0.4 | — |
| Reference electrode | — | — | — | — | 215.2 |

*Sample size was ¾" × ¾" in order to be able to compare with reference electrode.

As various changes could be made in the above constructions and methods without departing from the scope of the invention as defined in the claims, it is intended that all matter contained in the above description or shown in the accompanying drawings be interpreted as illustrative and not in a limiting sense.

The invention is not limited to these embodiments. The claims follow.

What is claimed is:

1. A skin-compatible, hot-melt processable, pressure sensitive adhesive, comprising:

between about 30 to 45 parts by weight of a copolymer comprised of between about 30 to 45 parts by weight of an (meth)acrylate ester monomer having C$_4$–C$_{20}$ alkyl chains, and between about 55 to 70 parts by weight of an acidic comonomer;

between about 0 to 35 parts by weight of a hydrophilic plasticizer;

between about 20 to 40 parts by weight of water, between about 0 to 3 parts by weight of a water soluble salt, between about 10 to 20 parts by weight of a surfactant, and between about 0.5 to 10 parts by weight of a polymer having amine functionality.

2. The adhesive according to claim 1 wherein the hydrophilic plasticizer is selected from the group consisting of polyethylene oxide, glycerin, and combinations thereof.

3. The adhesive according to claim 1 wherein the adhesive can be melt processed at a temperature between about 50° C. to 100° C.

4. The adhesive according to claim 3 wherein the adhesive can be melt processed at a temperature between about 55° C. to 85° C.

5. The adhesive of claim 1, wherein the (meth)acrylate monomer has a formula of

Formula (I)

wherein R$^1$ is H or CH$_3$, the latter corresponding to where the (meth)acrylate monomer is a methacrylate monomer, wherein R$^2$ is selected from the group consisting of linear, branched, aromatic, and cyclic hydrocarbon groups.

6. The adhesive of claim 1, wherein the (meth)acrylate monomer is selected from the group consisting of benzyl methacrylate, n-butyl acrylate, n-butyl methacrylate, cyclohexyl acrylate, cyclohexyl methacrylate, decyl acrylate, 2-ethoxy ethyl acrylate, 2-ethoxy ethyl methacrylate, 2-ethylhexyl acrylate, n-hexadecyl acrylate, n-hexadecyl methacrylate, hexyl acrylate, isoamyl acrylate, isobornyl acrylate, isobornyl methacrylate, isobutyl acrylate, isodecyl acrylate, isodecyl methacrylate, isononyl acrylate, isooctyl acrylate, isooctyl methacrylate, isotridecyl acrylate, lauryl acrylate, lauryl methacrylate, 2-methyl butyl acrylate, 4-methyl-2-pentyl acrylate, 1-methylcyclohexyl methacrylate, 2-methylcyclohexyl methacrylate, 3-methylcyclohexyl methacrylate, 4-methylcyclohexyl methacrylate, octadecyl acrylate, octadecyl methacrylate, n-octyl acrylate, n-octyl methacrylate, 2-phenoxy ethyl methacrylate, n-tetradecyl acrylate, n-tetradecyl methacrylate, and mixtures thereof.

7. The adhesive of claim 1, wherein the (meth)acrylate monomers are selected from the group consisting of n-butyl acrylate, 2-ethylhexyl acrylate, isooctyl acrylate, isononyl acrylate, isodecyl acrylate, and mixtures thereof.

8. The adhesive of claim 1, wherein the acidic comonomer is selected from the group consisting of ethylenically unsaturated carboxylic acids, ethylenically unsaturated sulfonic acids, ethylenically unsaturated phosphonic acids, and mixtures thereof.

9. The adhesive of claim 1, wherein the surfactant is selected from the group consisting of non(co)polymerizable nonionic surfactants, ethylenically-unsaturated copolymerizable nonionic surfactants, and mixtures thereof.

10. The adhesive of claim 1, wherein the polymer having amine functionality is selected from the group consisting of poly(vinyl amines), poly(allyl amines), poly(alkylene amines), poly(ethylenimine) and alkylated versions thereof, poly(vinyl pyridines), poly(vinyl pyrroles), poly(N-vinyl lactams), and homopolymers or copolymers from monomers of a formula of wherein
a is 0 or 1;
R is selected from H— and $CH_3$—,
X is selected from —O— and —NH—;
Y is a divalent linking group selected from the group consisting of groups having about 1 to about 5 carbon atoms and heteroatomic groups having at least one carbon atom and at least one atom of O, S, or N; and
Am is selected from the group consisting of pyridinyl or imidazolyl, and an amine fragment, primary, secondary or tertiary, of a formula:

wherein $R^1$ and $R^2$ are selected from H, alkyl, aryl, cycloalkyl, heterocyclic, and arenyl groups.

11. The adhesive of claim 1, wherein the polymer of amine functionality is poly(ethylenimine).

12. A method for preparing skin-compatible, hot-melt processable, pressure sensitive adhesive, comprising the steps of:
a) preparing a mixture of ethylenically unsaturated monomers comprising:
between about 30 to 45 parts by weight of an (meth) acrylate ester monomer having $C_4$–$C_{20}$ alkyl chains, and
between about 55 to 70 parts by weight of an acidic comonomer;
b) mixing between about 30 to 45 parts by weight of the mixture of ethylenically unsaturated monomers with between about 0 to 35 parts by weight of a hydrophilic plasticizer so as to form a hydrophilic plasticizer/monomer mixture;
c) polymerizing the monomers to form a polymer matrix containing the plasticizer;
d) blending an additive mixture into the polymer matrix, the additive mixture comprising
between about 20 to 40 parts by weight of water,
between about 0 to 3 parts of a water soluble salt,
between about 10 to 20 parts by weight of a surfactant, and
between about 0.5 to 10 parts by weight of a polymer having amine functionality, so as to form a skin-compatible hot-melt processible, ionically conductive, pressure sensitive adhesive.

13. A method for preparing skin-compatible, hot-melt processable, pressure sensitive adhesive, comprising the steps of:
a) preparing a mixture of ethylenically unsaturated monomers comprising:
between about 30 and about 45 parts by weight of an (meth)acrylate ester monomer having $C_4$–$C_{12}$ alkyl chains, and
between about 55 and about 70 parts by weight of an acidic comonomer;
b) mixing between about 30 and about 45 parts by weight of the mixture of ethylenically unsaturated monomers with between about 0 and about 35 parts by weight of a hydrophilic plasticizer, between about 10 and about 30 parts by weight of water, between about 0 and about 3 parts by weight of a water soluble salt, and between about 0 and about 7 parts by weight of a surfactant, so as to form a hydrophilic plasticizer/monomer/surfactant/water mixture;
c) polymerizing of the monomers to form a polymer matrix containing plasticizer, water, and surfactant;
d) blending an additive mixture into the polymer matrix, the additive mixture comprising
between about 1 and about 3 parts by weight of a water soluble salt,
between about 10 and about 30 parts by weight of water,
between about 10 and about 13 parts by weight of a surfactant, and
between about 0.5 and about 10 parts by weight of a polymer having amine functionality,
so as to form a skin-compatible hot-melt processable, ionically conductive, pressure sensitive adhesive.

14. The method according to claim 12 further comprising the step of melting the polymer matrix prior to the adding step so that the adding step forms the skin-compatible hot-melt processable, ionically conductive, pressure sensitive adhesive in a molten state.

15. The method according to claim 13 further comprising the step of melting the polymer matrix prior to the adding step so that the adding step forms the skin-compatible hot-melt processable, ionically conductive, pressure sensitive adhesive in a molten state.

16. The method according to claim 15 wherein the melting step is performed at a temperature between about 50° C. to 100° C.

17. The method according to claim 15 further comprising the step of dispensing the molten adhesive onto a backing.

18. A biomedical electrode, comprising:
a field of adhesive conductive medium according to claim 1 for contacting mammalian skin and a means for electrical communication for interfacing with the adhesive conductive medium and electrical diagnostic, therapeutic, or electrosurgical instrumentation, the adhesive conductive medium adhered to the means for electrical communication.

19. The biomedical electrode according to claim 18, wherein the means for electrical communication comprises a conductor member having an interface portion contacting the adhesive conductive medium and a tab portion available for mechanical and electrical contact with the electrical diagnostic, therapeutic, or electrosurgical instrumentation.

20. A pharmaceutical delivery device comprising: an adhesive layer for contacting mammalian skin and a backing layer, the adhesive layer adhered to the backing layer and comprising a pressure sensitive adhesive composition according to claim 1.

21. The pharmaceutical delivery device according to claim 20, wherein the adhesive layer further comprises a topical, transdermal, or iontophoretic therapeutic agent or pharmaceutical.

22. The pharmaceutical delivery device according to claim 20, wherein the adhesive layer further comprises an excipient, a solvent, or a penetration enhancing agent.

* * * * *